(12) United States Patent
Liu et al.

(10) Patent No.: US 8,871,968 B2
(45) Date of Patent: *Oct. 28, 2014

(54) PROCESS OF PRODUCING OXALATE BY CO GAS PHASE METHOD

(75) Inventors: Juntao Liu, Shanghai (CN); Fengxia Sun, Shanghai (CN); Jun Kuai, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 17 days.

This patent is subject to a terminal disclaimer.

(21) Appl. No.: 13/641,457

(22) PCT Filed: Apr. 13, 2011

(86) PCT No.: PCT/CN2011/000649
§ 371 (c)(1),
(2), (4) Date: Dec. 19, 2012

(87) PCT Pub. No.: WO2011/127752
PCT Pub. Date: Oct. 20, 2011

(65) Prior Publication Data
US 2013/0197265 A1   Aug. 1, 2013

(30) Foreign Application Priority Data
Apr. 15, 2010 (CN) .......................... 2010 1 0146999

(51) Int. Cl.
| | | |
|---|---|---|
| C07C 67/18 | (2006.01) | |
| C07C 67/36 | (2006.01) | |
| B01J 23/89 | (2006.01) | |
| B01J 23/656 | (2006.01) | |
| B01J 21/04 | (2006.01) | |
| B01J 21/06 | (2006.01) | |

(52) U.S. Cl.
CPC .................. C07C 67/18 (2013.01); B01J 21/04 (2013.01); B01J 21/063 (2013.01); C07C 67/36 (2013.01); B01J 23/8973 (2013.01); B01J 23/8926 (2013.01); B01J 23/8946 (2013.01); B01J 23/6562 (2013.01); B01J 23/894 (2013.01)
USPC ....................................................... 560/204

(58) Field of Classification Search
None
See application file for complete search history.

(56) References Cited

U.S. PATENT DOCUMENTS 4,629,806 A * 12/1986 Cleveland et al. ............ 560/204
2011/0257425 A1* 10/2011 Liu et al. ....................... 558/488

FOREIGN PATENT DOCUMENTS

| CN | 1048098 | 12/1990 |
| CN | 1772600 | 5/2006 |
| CN | 201770631 | * 3/2011 |
| EP | 0 401 600 | 12/1990 |
| JP | 2004091484 | * 3/2004 |

OTHER PUBLICATIONS

Machine tranlation of CN 201770631 U.*
Machine translation of JP2004091484.*

* cited by examiner

*Primary Examiner* — Brandon Fetterolf
*Assistant Examiner* — Ana Z Muresan
(74) *Attorney, Agent, or Firm* — Novick, Kim & Lee, PLLC; Allen Xue

(57) ABSTRACT

The present invention relates to a process of producing oxalate by CO gas phase method for chiefly solving the technical problem of the low utilization efficiency of nitrogen oxides or nitrous acid esters in the prior art. The present invention solves the problem in a better way by using the following steps including: a gas phase stream V containing NO and methanol and oxygen enter a supergravity rotating bed reactor II and are subjected to the oxidative esterification reaction to produce an effluent VI containing methyl nitrite; a methyl nitrite effluent VII obtained from separating said effluent VI together with a CO gas II enter a coupling reactor II and is contacted with a catalyst II to react to form a dimethyl oxalate effluent VIII and a gas phase effluent IX containing NO; the resultant dimethyl oxalate effluent VIII is separated to obtain a dimethyl oxalate product I; optionally, the gas phase effluent IX containing NO is returned to the step above so as to be mixed with the gas phase stream V containing NO for being recycled. Therefore, the process is applicable to the industrial production of oxalate by CO gas phase method.

19 Claims, No Drawings

PROCESS OF PRODUCING OXALATE BY CO GAS PHASE METHOD

CROSS REFERENCE TO RELATED APPLICATIONS

This is a U.S. national stage entry of International Application No. PCT/CN2011/000649, filed on Apr. 13, 2011, which in turn claims priority to Chinese Patent Application No. 201010146999.2, filed Apr. 15, 2010, each of which is hereby incorporated by reference herein in its entirety.

TECHNICAL FIELD

The present invention relates to a process of producing oxalate by CO gas phase method, especially, to a process of the production of dimethyl oxalate by CO coupling, as well as the co-production of diethyl oxalate, dipropyl oxalate or dibutyl oxalate, the consumption of nitrogen oxides or nitrous acid esters being greatly reduced.

Oxalate is the important raw material in the organic chemical industry, which is used on a large scale for producing various dyes, medicines, important solvents, extracting agents and various intermediates in the industry of fine chemicals. Upon the advent of the $21^{st}$ century, as the environmentally friendly biodegradable engineering plastic monomer, oxalate is widely valued in the international world. Besides, the hydrolysis of oxalate at normal temperature can produce oxalic acid and the aminolysis at normal temperature can produce oxamide which is a high-quality and slow-releasing fertilizer. Oxalate can also be used as solvents and for producing the intermediates of medicines and dyes etc., for example the various condensation reactions between oxalate and fatty acid esters, cyclohexyl acetyl benzene, amino alcohols and many heterocyclic compounds can be carried out. Oxalate can also be used for synthesizing thymine used as hormone in medicine. Besides, the hydrogenation of oxalate at low pressure can produce ethylene glycol which is a significant raw material in the chemical industry. However, currently, the production of ethylene glycol primarily relies on the petroleum route at high cost. China needs an enormous amount of imported ethylene glycol each year. In 2007, the import quantum is almost 4.8 million tons.

The traditional production method of oxalate is to utilize oxalic acid by the esterification thereof with alcohols. This producing technique is expensive in terms of costs, consumes great energy and results in a heavy pollution and an unreasonable use of raw materials. For many years, people are seeking for a low cost, environmentally friendly process route. In the sixties of last century, D. F. Fenton from Unocal Corp of USA found that CO, alcohol and oxygen can be used to directly synthesize dialkyl oxalate by the oxidative carbonylation reation. Since then, Ube Industries from Japan and American Atlantic Richfield Company (ARCO) successively carried out researches and developments in this field.

In terms of the developmental course, the processes of synthesizing oxalate by CO oxidative coupling method can be divided into two processes, namely the liquid phase method and the gas phase method. The conditions of synthesizing oxalate by CO liquid phase method are comparatively stringent as the reaction is carried out at high pressure and the liquid phase system thereby tends to corrode the equipment and the catalyst during the reaction tends to run off. The CO coupling gas phase method of producing oxalate is the most advantageous. Abroad, Ube Industries and Montedison from Italy successively carried out the researches on the gas phase method in 1978, wherein Ube Industries developed the technology of gas phase catalytic synthesis of oxalate at a reaction pressure of 0.5 MPa and a temperature of 80° C.~150° C.

The reaction course of synthesizing oxalate is as follows:

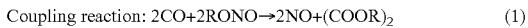

Coupling reaction: $2CO+2RONO \rightarrow 2NO+(COOR)_2$     (1)

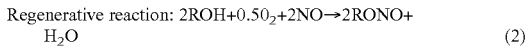

Regenerative reaction: $2ROH+0.5O_2+2NO \rightarrow 2RONO+H_2O$     (2)

It is evident from the course above that theoretically, this system does not consume NO or RONO (alkyl nitrite), but actually, during the reaction of step (2), in addition to the production of RONO as the primary product, side reactions often occur, especially the production of dilute nitric acid as the by-product. This must consume more NO gas. Thus, NO must be incessantly supplemented to the reaction system so that the catalytic reaction of synthesizing oxalate can go on stably and continuously for a long time. Under usual situations, NO comes from the products of ammonia oxidation or the end gases of nitric acid. However, the products of ammonia oxidation or the end gases of nitric acid, besides NO or $NO_2$ as required, further comprise the gases such as $N_2$, Ar, and He, which are nonreactive and difficult to be condensed. If a large amount of the said gases enter the system of synthesizing oxalate, said gases will be very adverse to the catalytic reaction of synthesizing oxalate, or even stop the reaction. The successful reaction can only be guaranteed when these nonreactive gases are discharged from the reaction system. Nevertheless, when the gases such as $N_2$, Ar, and He, which are nonreactive and difficult to be condensed are discharged from the reaction system, the useful reactive substances in the synthetic reaction system such as NO and RONO will be also taken out at the same time. In that case, the raw materials are wasted and the environment is polluted. Thus, NO and RONO must be effectively recovered and the treatment of eliminating the environmental pollution must be carried out. It can thus be seen that the key points of increasing the low efficiency of utilizing nitrogen oxides or nitrous acid esters are that on the one hand, the occurrences of the side reactions (e.g., the reaction of generating nitric acid) during the reaction course (including the reaction of introducing nitrogen oxides or nitrous acid esters into the system and the normal cyclic reaction course) should be reduced, and meanwhile, the losses of the materials of nitrogen oxides or nitrous acid esters taken out by the incondensable gases should be reduced to the utmost extent.

Chinese Patent No. CN1048098A utilized the method of combining compression and condensation to accomplish this task, but the operation conditions required by the patent were comparatively stringent and the effects were poor. Patent CN200510107783.4 further improved CN1048098A and disclosed a new production method of synthesizing oxalate by using NO. Firstly, alcohols were primarily used to absorb a large amount of nitrous acid esters. Then, the method of combining compression and condensation was used to condense the small amount of alcohols and nitrous acid esters in the gas phase into liquids at a pressure of 0.1~10 MPa and a condensation temperature of −20° C.~100° C. The alcohols and the nitrous acid esters and the incondensable gases were separated, and then the recovered condensed liquids were recycled and the incondensable gases were discharged. Obviously, the method also suffers from the problem of the strict operation conditions and meanwhile the high costs of operation energy and the low utilization efficiency of nitrogen oxides or nitrous acid esters.

The supergravity technology is a new technology of enhancing the multiphase flow delivery and reaction course. Since the technology came out in the last century, it has been widely valued both domestically and abroad. Because it has the wide applicability and the advantages of small volume, light weight, low energy consumption, easy operation, easy maintenance, safety, reliability, flexibility and being more adaptive to environment etc. which the traditional instruments do not possess, the commercializing application of the supergravity technology in the industrial fields like environmental protection, the chemical industries of materials and biology is very encouraging. However, at present, the supergravity technology is primarily at the stage of the development of applications thereof. Moreover, the use of the supergravity rotating bed reactor in the production of $C_1$-$C_4$ alkyl nitrites and thereby the production of oxalate are not reported yet.

SUMMARY OF THE INVENTION

The technical problem solved by the present invention is the one of the low utilization efficiency of nitrogen oxides or nitrous acid esters in the prior art, and provides a new process of producing oxalate by CO gas phase method, which has the advantages of the high utilization efficiency of nitrogen oxides or nitrous acid esters For solving the technical problem above, the technical solution used in the present invention is as follows:

A process of producing oxalate by CO gas phase method comprises the following steps:

c) a gas phase stream V containing NO and methanol and oxygen enter a supergravity rotating bed reactor II and are subjected to the oxidative esterification reaction to produce an effluent VI containing methyl nitrite; a methyl nitrite effluent VII obtained from separating said effluent VI, together with a CO gas II, enter a coupling reactor II and is contacted with a catalyst II to react to form a dimethyl oxalate effluent VIII and a gas phase effluent IX containing NO; the resultant dimethyl oxalate effluent VIII is separated to obtain a dimethyl oxalate product I;

d) optionally, the gas phase effluent IX containing NO is returned to step c) so as to be mixed with the gas phase stream V containing NO for being recycled;

wherein, the rotor of the supergravity rotating bed reactor II is attached with a porous filler layer; the catalyst II is a Pd-containing catalyst with a Pd amount of 0.01~1% based on the simple substance, relative to the weight of the catalyst carrier.

In one preferred embodiment, the aforesaid gas phase stream V containing NO is obtained in steps a) and b) prior to step c) in accordance with the following manner:

a) a nitride oxide mixture and $C_2$-$C_4$ alkanol and air or oxygen firstly enter a supergravity rotating bed reactor Ito produce an effluent I comprising $C_2$-$C_4$ alkyl nitrite; the incondensable gas effluent II and the effluent III of $C_2$-$C_4$ alkyl nitrite are obtained by separating said effluent I;

b) the effluent III of $C_2$-$C_4$ alkyl nitrite and a CO gas I enter a coupling reactor I so as to be contacted with a catalyst Ito react to form an oxalate liquid phase effluent IV and a gas phase stream V containing NO; the oxalate liquid phase effluent IV as formed is separated to obtain an oxalate product II.

In a more preferred embodiment in terms of the aforesaid preferred embodiment, the rotor of the supergravity rotating bed reactor I is attached with a porous filler layer; the molar ratio of the CO gas II to the CO gas I is 5~300:1; the catalyst I is a Pd-containing catalyst with a Pd amount of 0.01~1% based on the simple substance, relative to the weight of the catalyst carrier.

Therein, the operation conditions of the supergravity rotating bed reactor I in the aforesaid technical solution are preferably: a reaction temperature of 20~100° C., a reaction pressure of −0.05~2.0 MPa, a reaction contacting time of 0.05~300 s, a molar ratio of nitride oxide mixture and $C_2$-$C_4$ alkanol and oxygen in air or oxygen of 1:1~50:0.2~0.3; the more preferred operation conditions of the supergravity rotating bed reactor I are: a reaction temperature of 30~70° C., a reaction pressure of 0.01~1.0 MPa, a reaction contacting time of 1~200 s, a molar ratio of nitride oxide mixture and $C_2$-$C_4$ alkanol and oxygen in air or oxygen of 1:1~20:0.22~0.28. The operation conditions of the supergravity rotating bed reactor II are preferably: a reaction temperature of 20~100° C., a reaction pressure of −0.05~2.0 MPa, a reaction contacting time of 0.05~300 s, a molar ratio of NO in the gas phase stream V containing NO to methanol and oxygen of 1:1~50: 0.01~0.25; the more preferred operation conditions of the supergravity rotating bed reactor II are: a reaction temperature of 25~70° C., a reaction pressure of 0.05~1.0 MPa, a reaction contacting time of 1~200 s, a molar ratio of NO in the gas phase stream V containing NO to methanol and oxygen of 1:1~20:0.1~0.25.

The operation conditions of the coupling reactor I in the aforesaid technical solution are preferably: a reaction temperature of 80~160° C., a reaction contacting time of 0.1~100 s, a reaction pressure of −0.05~2.0 MPa, a molar ratio of the CO gas Ito $C_2$-$C_4$ alkyl nitrite of 1.1~15:1; the more preferred operation conditions of the coupling reactor I are: a reaction temperature of 90~150° C., a reaction contacting time of 0.5~50 s, a reaction pressure of 0.01~1.0 MPa, a molar ratio of the CO gas I to $C_2$-$C_4$ alkyl nitrite of 1.1~10:1. The operation conditions of the coupling reactor II are preferably: a reaction temperature of 80~160° C., a reaction contacting time of 0.1~100 s, a reaction pressure of −0.05~2.0 MPa, a molar ratio of the CO gas II to the methyl nitrite effluent VII of 1.1~10:1; the more preferred operation conditions of the coupling reactor II are: a reaction temperature of 90~150° C., a reaction contacting time of 0.5~50 s, a reaction pressure of 0.01~1.0 MPa, a molar ratio of the CO gas II to the methyl nitrite effluent VII of 1.1~5:1.

The nitride oxide mixture in the technical solution above is preferably selected from the products of ammonia oxidation and the end gases of nitric acid or is preferably obtained by reacting nitrites with sulphuric acid or nitric acid or by decomposing nitric acid. The more preferred embodiment of the nitride oxide mixture is that the mixture is selected from the products of ammonia oxidation; the $C_2$-$C_4$ alkanol is selected from ethanol, propanol and butanol; the molar ratio of the CO gas II to the CO gas I is preferably in the range of 10~200:1.

The active components of the catalyst I and the catalyst II in the technical solution above are both Pd, preferably in an amount range of 0.01~0.8% of the weight of the catalyst carrier, based on the simple substance, more preferably in an amount range of 0.02~0.6% of the weight of the catalyst carrier. The catalyst I and the catalyst II further comprise the optional adjuvants and carriers. The adjuvants are selected from at least one of alkali metals, alkaline earth metals or the compounds of transition metal elements, in an amount of 0.01~15%, preferably 1~10% of the weight of the catalyst based on the metal simple substance. The adjuvants are preferably selected from at least one of the compounds of K, Fe, Bi, Cu, Zr, Ba, Mn, Mg, Ce and Sn, in an amount range of 0.05~10%, preferably 1~7% of the weight of the catalyst based on the metal simple substance. The carriers are selected from at least one of alumina, molecular sieve, titanium oxide, magnesium oxide, calcium oxide, and preferably selected from α-$Al_2O_3$.

It is well-known that during the two-step reaction process of preparing ethylene glycol by synthesis gas, the selection of the CO coupling route of producing oxalate is very important. In view of the practical industrial applications, it is generally thought that the technical route of firstly producing dimethyl oxalate by CO coupling, and then hydrogenating dimethyl oxalate to produce ethylene glycol is the most feasible. However, the CO coupling reaction course needs to consume NO. Therefore, during supplementing the NO raw material to the process of producing dimethyl oxalate by CO coupling, under general situations, methanol, oxygen and NO are used to be subjected to oxidative esterification, and then the nonreactive gases are exhausted by the method of combining compression, condensation and alcohol absorption, and then methyl nitrite resulting from NO reaction is introduced into the system and reacted. However, the encountered problem is that the boiling point (−16.5° C.) of methyl nitrite is rather low, and methyl nitrite is a gas at the normal temperature. Thus, the method of combining compression, condensation and alcohol absorption should be used, resulting in the high costs of operation energy and the poor effects. Nevertheless, in, e.g., one embodiment of the present invention, an oxidative esterification reactor I and the coupling reaction I are introduced into the NO supplementing system, and thereby ethanol, propanol or butanol are firstly subjected to oxidative esterification with oxygen and NO to produce ethyl nitrite, propyl nitrite or butyl nitrite; then the nonreactive inert components introduced into the nitride oxide as the raw material are directly exhausted by simple separation or further treated; then the amount of nitride oxides or nitrous acid esters in the exhausted gases can be restricted to below a comparatively low amount; next, ethyl nitrite (a boiling point of 15° C.), propyl nitrite (a boiling point of 39° C.) or butyl nitrite (a boiling point of 75° C.) and the CO gas I are fed into the coupling reactor Ito be subjected to the coupling reaction so as to produce diethyl oxalate, dipropyl oxalate or dibutyl oxalate; meanwhile, the reaction releases NO; NO from the reaction and unreacted CO and the newly supplemented oxygen and methanol enter the reactor II to produce methyl nitrite; then compression and condensation are no longer required; after separation is carried out by directly using the conventional pressure or temperature, methyl nitrite is mixed with the CO gas II and fed into the coupling reactor II to continue the reaction; NO resulting from the reaction directly enters the entrance of the reactor II for being recycled; the coupling reactor II is the primary reactor of the coupling reaction course, and the coupling reactor I is the reactor of the NO supplementing system performing the assistant function; most of the CO raw materials are reacted through the reactor II to produce dimethyl oxalate. Researchers found that the oxidative esterification of nitride oxides with oxygen and alcohols to produce alkyl nitrite is a quick reaction, while the side reactions of generating nitric acid etc. are slightly slower. The reaction rate of the oxidative esterification course of NO is mainly affected by the resistance of gas-liquid mass transfer. If the gas-liquid mass transfer efficiency is effectively increased, the probability of generating $N_2O_4$ can be further effectively reduced, thereby further reducing the losses of nitride oxides or nitrous acid esters. On the basis of the sufficient studies of the features of the oxidative esterification of nitride oxides and oxygen and alcohols, the technical solution of the present invention further proposes the use of the supergravity rotating bed reactor as the reactor of oxidative esterification for fully utilizing the prominent advantage possessed by the supergravity rotating bed reactor which can exponentially increase the gas-liquid mass transfer efficiency and furthermore more effectively promoting the primary reaction and greatly inhibiting the occurrences of side reactions, thereby increasing the utilization efficiencies of the raw materials like NO. In a word, the present invention adequately makes use of the differences of the boiling points of distinct nitrous acid esters and fully utilizes the advantage of the high efficient mass transfer of the supergravity rotating bed reactor, so that the high yield and the high selectivity of the coupling reaction are ensured and meanwhile, the losses of nitride oxides or nitrous acid esters are dramatically reduced, the utilization efficiency of nitride oxides or nitrous acid esters is increased, and the environmental pollution is decreased.

For example, by using the technical solution of the present invention, the nitride oxide mixture and $C_2$-$C_4$ alkanol and air firstly enter a supergravity rotating bed reactor Ito produce an effluent I comprising $C_2$-$C_4$ alkyl nitrite; an incondensable gas effluent II and an effluent III of $C_2$-$C_4$ alkyl nitrite are obtained by separating said effluent I; the effluent III of $C_2$-$C_4$ alkyl nitrite and a CO gas I enter a coupling reactor I so as to be contacted with a catalyst Ito react to form an oxalate liquid phase effluent IV and a gas phase stream V containing NO; the gas phase stream V containing NO and methanol and oxygen enter a supergravity rotating bed reactor II and are subjected to the oxidative esterification reaction to produce an effluent VI containing methyl nitrite; the methyl nitrite effluent VII obtained from separating said effluent VI, together with a CO gas II, enter a coupling reactor II and is contacted with a catalyst II to react to form a dimethyl oxalate effluent VIII and a gas phase effluent IX containing NO; optionally, the gas phase effluent IX containing NO is mixed with the gas phase stream V containing NO for being recycled. Therein, the molar ratio of the CO gas II to the CO gas I is in the range of 10~200:1; nitride oxides are selected from the products of ammonia oxidation; the $C_2$-$C_4$ alkanol is selected from ethanol, propanol and butanol; the catalyst I and the catalyst II are both selected from Pd-containing catalysts with a Pd amount of 0.01~1% based on the simple substance, relative to the weight of the catalyst carrier. The rotors of the supergravity rotating bed reactors I and II are both attached with a porous filler layer. The operation conditions of the supergravity rotating bed reactor I are: a reaction temperature of 30~70° C., a reaction pressure of 0.01~1.0 MPa, a reaction contacting time of 1~200 s, a molar ratio of nitride oxide mixture and $C_2$-$C_4$ alkanol and oxygen in air or oxygen of 1:1~50:0.2~0.3; the operation conditions of the supergravity rotating bed reactor II are: a reaction temperature of 25~70° C., a reaction pressure of 0.05~1.0 MPa, a reaction contacting time of 1~200 s, a molar ratio of NO in the gas phase stream V containing NO to methanol and oxygen of 1:1~20:0.1~0.25; the operation conditions of the coupling reactor I are: a reaction temperature of 90~150° C., a reaction contacting time of 0.5~50 s, a reaction pressure of 0.01~1.0 MPa, a molar ratio of the CO gas I to $C_2$-$C_4$ alkyl nitrite of 1.1~10:1; the operation conditions of the coupling reactor I are: a reaction temperature of 90~150° C., a reaction contacting time of 0.5~50 s, a reaction pressure of 0.01~1.0 MPa, a molar ratio of the CO gas II to the methyl nitrite effluent VII of f 1.1~5:1. The results under the aforesaid conditions are: the NO utilizing efficiency can be greater than 98%, preferably greater than 99%. Thus, the excellent technical effects are obtained.

The following are the further demonstrations of the present invention by examples, but the invention is not limited by the examples.

DETAILED DESCRIPTION OF THE INVENTION AND EXAMPLES

Example 1

A mixture gas comprising NO from ammonia oxidation (the amount of NO being 90% by volume, and the amount of nitrogen being 10% by volume) and ethanol and oxygen firstly enter a supergravity rotating bed reactor I to produce an effluent I comprising ethyl nitrite; an incondensable gas effluent II (including $N_2$) and an effluent III of ethyl nitrite are obtained by separating said effluent I; the effluent III of ethyl nitrite and a CO gas I enter a coupling reactor I so as to be contacted with a catalyst I to form an diethyl oxalate liquid phase effluent IV and a gas phase stream V containing NO; the gas phase stream V containing NO and methanol and oxygen enter a supergravity rotating bed reactor II and are subjected to the oxidative esterification reaction to produce an effluent VI containing methyl nitrite; a methyl nitrite effluent VII obtained from separating said effluent VI together with a CO gas II enter a coupling reactor II and is contacted with a catalyst II to react to form a dimethyl oxalate effluent VIII and a gas phase effluent IX containing NO; the gas phase effluent IX containing NO is mixed with the gas phase stream V containing NO for being recycled. Therein, the molar ratio of the CO gas II to the CO gas I is 150:1; the catalyst I and the catalyst II both select Pd as the active component, and the constitutions thereof by weight are both 0.45% Pd+0.40% K+0.22%Fe/α-$Al_2O_3$; the operation conditions of the supergravity rotating bed reactor I are: a reaction temperature of 40° C., a reaction pressure of 0.01 MPa, a reaction contacting time of 50 s, a molar ratio of NO and ethanol and oxygen of 1:20:0.25; the operation conditions of the supergravity rotating bed reactor II are: a reaction temperature of 30° C., a reaction pressure of 0.01 MPa, a reaction contacting time of 20 s, a molar ratio of NO in the gas phase stream V containing NO to methanol and oxygen of 1:5:0.18; the operation conditions of the coupling reactor I are: a reaction temperature of 98° C., a reaction contacting time of 3 s, a reaction pressure of 0.01 MPa, a molar ratio of the CO gas I to ethyl nitrite of 3:1; the operation conditions of the coupling reactor II are: a reaction temperature of 120° C., a reaction contacting time of 5 s, a reaction pressure of 0.01 MPa, a molar ratio of the CO gas II to the methyl nitrite effluent VII of 3:1. The results under the aforesaid conditions are: an NO utilizing efficiency of 99.4%, an amount of nitride oxides in the exhausted end gases of 20 ppm, a space time yield of dimethyl oxalate of 890 g/(h·L), and a selectivity of dimethyl oxalate of 98.2%.

Example 2

The procedures according to Example 1, but wherein: the molar ratio of the CO gas II to the CO gas I is 100:1; the catalyst I and the catalyst II both select Pd as the active component, and the constitutions thereof by weight are both 0.30% Pd+0.2% Bi+0.02% Fe/α-$Al_2O_3$. The $C_2$-$C_4$ alkanol is selected from ethanol. The operation conditions of the supergravity rotating bed reactor I are: a reaction temperature of 70° C., a reaction pressure of 0.5 MPa, a reaction contacting time of 150 s, a molar ratio of NO and ethanol and oxygen of 1:20:0.26; the operation conditions of the supergravity rotating bed reactor II are: a reaction temperature of 45° C., a reaction pressure of 0.4 MPa, a reaction contacting time of 30 s, a molar ratio of NO in the gas phase stream V containing NO to methanol and oxygen of 1:25:0.20; the operation conditions of the coupling reactor I are: a reaction temperature of 150° C., a reaction contacting time of 40 s, a reaction pressure of 0.1 MPa, a molar ratio of the CO gas I to ethyl nitrite of 5:1; the operation conditions of the coupling reactor II are: a reaction temperature of 140° C., a reaction contacting time of 2 s, a reaction pressure of 0.2 MPa, a molar ratio of the CO gas II to the methyl nitrite effluent VII of 5:1. The results under the aforesaid conditions are: an NO utilizing efficiency of 99.6%, an amount of nitride oxides in the exhausted end gases of 25 ppm, a space time yield of dimethyl oxalate of 980 g/(h·L), and a selectivity of dimethyl oxalate of 98.6%.

Example 3

The procedures according to Example 1, but wherein: the molar ratio of the CO gas II to the CO gas I is 150:1; the constitution of the catalyst I by weight is 0.30% Pd+0.2% Bi+0.02% Fe/α-$Al_2O_3$; the constitution of the catalyst II by weight is 0.6% Pd+0.2% Cu+0.08% Fe/α-$Al_2O_3$. The $C_2$-$C_4$ alkanol is selected from n-butanol. The operation conditions of the supergravity rotating bed reactor I are: a reaction temperature of 50° C., a reaction pressure of −0.02 MPa, a reaction contacting time of 30 s, a molar ratio of NO and n-butanol and oxygen of 1:10:0.27; the operation conditions of the supergravity rotating bed reactor II are: a reaction temperature of 60° C., a reaction pressure of 0.2 MPa, a reaction contacting time of 10 s, a molar ratio of NO in the gas phase stream V containing NO to methanol and oxygen of 1:15:0.20; the operation conditions of the coupling reactor I are: a reaction temperature of 130° C., a reaction contacting time of 5 s, a reaction pressure of 0.3 MPa, a molar ratio of the CO gas I to butyl nitrite of 5:1; the operation conditions of the coupling reactor II are: a reaction temperature of 130° C., a reaction contacting time of 5 s, a reaction pressure of 0.3 MPa, a molar ratio of the CO gas II to the methyl nitrite effluent VII of 2:1. The results under the aforesaid conditions are: an NO utilizing efficiency of 99.1%, an amount of nitride oxides in the exhausted end gases of 30 ppm, a space time yield of dimethyl oxalate of 1100 g/(h·L), and a selectivity of dimethyl oxalate of 98.2%.

Example 4

The procedures according to Example 1, but wherein: the molar ratio of the CO gas II to the CO gas I is 30:1; the constitution of the catalyst I by weight is 0.8% Pd+10% Ce+0.003% Zr+0.507% Fe/$TiO_2$; the constitution of the catalyst II by weight is 0.6% Pd+0.2% Cu+0.08% Fe/α-$Al_2O_3$. The $C_2$-$C_4$ alkanol is selected from n-propanol. The operation conditions of the supergravity rotating bed reactor I are: a reaction temperature of 60° C., a reaction pressure of 1.5 MPa, a reaction contacting time of 5 s, a molar ratio of NO and n-propanol and oxygen of 1:5:0.25; the operation conditions of the supergravity rotating bed reactor II are: a reaction temperature of 45° C., a reaction pressure of 1.5 MPa, a reaction contacting time of 3 s, a molar ratio of NO in the gas phase stream V containing NO to methanol and oxygen of 1:3:0.23; the operation conditions of the coupling reactor I are: a reaction temperature of 110° C., a reaction contacting time of 2 s, a reaction pressure of 0.01 MPa, a molar ratio of the CO gas I to propyl nitrite of 8:1; the operation conditions of the coupling reactor II are: a reaction temperature of 125° C., a reaction contacting time of 2 s, a reaction pressure of 0.03 MPa, a molar ratio of the CO gas II to the methyl nitrite effluent VII of 1.5:1. The results under the aforesaid conditions are: an NO utilizing efficiency of 99.3%, an amount of nitride oxides in the exhausted end gases of 12 ppm, a space time yield of dimethyl oxalate of 1020 g/(h·L), and a selectivity of dimethyl oxalate of 98.6%.

Example 5

The procedures according to Example 1, but wherein: the molar ratio of the CO gas II to the CO gas I is 80:1; the constitution of the catalyst I by weight is 0.8% Pd+10% Ce+0.003% Zr+0.507% Fe/$TiO_2$; the constitution of the catalyst II by weight is 0.6% Pd+0.2% Cu+0.08% Fe/α-Al$_2$O$_3$. The C$_2$-C$_4$ alkanol is selected from ethanol. The operation conditions of the supergravity rotating bed reactor I are: a reaction temperature of 30° C., a reaction pressure of 1.0 MPa, a reaction contacting time of 50 s, a molar ratio of NO and ethanol and oxygen of 1:8:0.25; the operation conditions of the supergravity rotating bed reactor II are: a reaction temperature of 45° C., a reaction pressure of 0.01 MPa, a reaction contacting time of 0.8 s, a molar ratio of NO in the gas phase stream V containing NO to methanol and oxygen of 1:6:0.22; the operation conditions of the coupling reactor I are: a reaction temperature of 160° C., a reaction contacting time of 120 s, a reaction pressure of 0.01 MPa, a molar ratio of the CO gas I to ethyl nitrite of 12:1; the operation conditions of the coupling reactor II are: a reaction temperature of 125° C., a reaction contacting time of 3 s, a reaction pressure of 0.03 MPa, a molar ratio of the CO gas II to the methyl nitrite effluent VII of 1.3:1. The results under the aforesaid conditions are: an NO utilizing efficiency of 99.5%, an amount of nitride oxides in the exhausted end gases of 18 ppm, a space time yield of dimethyl oxalate of 920 g/(h·L), and a selectivity of dimethyl oxalate of 99.1%.

Example 6

The procedures according to Example 1, but wherein: the molar ratio of the CO gas II to the CO gas I is 60:1; the constitution of the catalyst I by weight is 0.11% Pd+0.6% Ba+0.2% Fe/MgO; the constitution of the catalyst II by weight is 0.34% Pd+1.0% K+0.46% Mn/α-Al$_2$O$_3$. The C$_2$-C$_4$ alkanol is selected from ethanol. The operation conditions of the supergravity rotating bed reactor I are: a reaction temperature of 25° C., a reaction pressure of 0.2 MPa, a reaction contacting time of 15 s, a molar ratio of NO and ethanol and oxygen of 1:6:0.26; the operation conditions of the supergravity rotating bed reactor II are: a reaction temperature of 55° C., a reaction pressure of 0.05 MPa, a reaction contacting time of 2.5 s, a molar ratio of NO in the gas phase stream V containing NO to methanol and oxygen of 1:4:0.18; the operation conditions of the coupling reactor I are: a reaction temperature of 100° C., a reaction contacting time of 4 s, a reaction pressure of 0.01 MPa, a molar ratio of the CO gas I to ethyl nitrite of 4:1; the operation conditions of the coupling reactor II are: a reaction temperature of 135° C., a reaction contacting time of 2 s, a reaction pressure of 0.03 MPa, a molar ratio of the CO gas II to the methyl nitrite effluent VII of 1.4:1. The results under the aforesaid conditions are: an NO utilizing efficiency of 98.9%, an amount of nitride oxides in the exhausted end gases of 25 ppm, a space time yield of dimethyl oxalate of 986 g/(h·L), and a selectivity of dimethyl oxalate of 99.3%.

Example 7

The procedures according to Example 1, but wherein: the molar ratio of the CO gas II to the CO gas I is 120:1; the constitution of the catalyst I by weight is 0.32% Pd+0.25% Fe/α-Al$_2$O$_3$; the constitution of the catalyst II by weight is 0.34% Pd+1.0% K+0.46% Mn/α-Al$_2$O$_3$. The C$_2$-C$_4$ alkanol is selected from n-butanol. The operation conditions of the supergravity rotating bed reactor I are: a reaction temperature of 65° C., a reaction pressure of 0.8 MPa, a reaction contacting time of 100 s, a molar ratio of NO and n-butanol and oxygen of 1:12:0.24; the operation conditions of the supergravity rotating bed reactor II are: a reaction temperature of 48° C., a reaction pressure of 0.1 MPa, a reaction contacting time of 12 s, a molar ratio of NO in the gas phase stream V containing NO to methanol and oxygen of 1:8:0.24; the operation conditions of the coupling reactor I are: a reaction temperature of 140° C., a reaction contacting time of 80 s, a reaction pressure of 0.2 MPa, a molar ratio of the CO gas I to butyl nitrite of 10:1; the operation conditions of the coupling reactor II are: a reaction temperature of 145° C., a reaction contacting time of 5 s, a reaction pressure of 0.03 MPa, a molar ratio of the CO gas II to the methyl nitrite effluent VII of 1.2:1. The results under the aforesaid conditions are: an NO utilizing efficiency of 99.2%, an amount of nitride oxides in the exhausted end gases of 5 ppm, a space time yield of dimethyl oxalate of 1041 g/(h·L), and a selectivity of dimethyl oxalate of 98.7%.

Example 8

The procedures according to Example 1, but wherein: the molar ratio of the CO gas II to the CO gas I is 10:1; the constitution of the catalyst I by weight is 0.41% Pd+0.82% Fe/α-Al$_2$O$_3$; the constitution of the catalyst II by weight is 0.22% Pd+1.0% Mg+2.10% Mn/α-Al$_2$O$_3$. The C$_2$-C$_4$ alkanol is selected from n-propanol. The operation conditions of the supergravity rotating bed reactor I are: a reaction temperature of 48° C., a reaction pressure of 1.8 MPa, a reaction contacting time of 45 s, a molar ratio of NO and n-propanol and oxygen of 1:30:0.23; the operation conditions of the supergravity rotating bed reactor II are: a reaction temperature of 45° C., a reaction pressure of 0.01 MPa, a reaction contacting time of 3 s, a molar ratio of NO in the gas phase stream V containing NO to methanol and oxygen of 1:3:0.20; the operation conditions of the coupling reactor I are: a reaction temperature of 150° C., a reaction contacting time of 3 s, a reaction pressure of 0.05 MPa, a molar ratio of the CO gas I to propyl nitrite of 5:1; the operation conditions of the coupling reactor II are: a reaction temperature of 148° C., a reaction contacting time of 6 s, a reaction pressure of 0.05 MPa, a molar ratio of the CO gas II to the methyl nitrite effluent VII of 2:1. The results under the aforesaid conditions are: an NO utilizing efficiency of 99.4%, an amount of nitride oxides in the exhausted end gases of 10 ppm, a space time yield of dimethyl oxalate of 1011 g/(h·L), and a selectivity of dimethyl oxalate of 99.0%.

Example 9

The procedures according to Example 1, but wherein: the molar ratio of the CO gas II to the CO gas I is 10:1; the constitution of the catalyst I by weight is 0.12% Pd+0.33% Fe/α-Al$_2$O$_3$; the constitution of the catalyst II by weight is 0.52% Pd+1.5% Mg+2.30% Mn/α-Al$_2$O$_3$. The C$_2$-C$_4$ alkanol is selected from n-butanol. The operation conditions of the supergravity rotating bed reactor I are: a reaction temperature of 53° C., a reaction pressure of 0.2 MPa, a reaction contacting time of 18 s, a molar ratio of NO and n-butanol and oxygen of 1:5:0.20; the operation conditions of the supergravity rotating bed reactor II are: a reaction temperature of 50° C., a reaction pressure of 0.01 MPa, a reaction contacting time of 4 s, a molar ratio of NO in the gas phase stream V containing NO to methanol and oxygen of 1:8:0.20; the operation conditions of the coupling reactor I are: a reaction temperature of 95° C., a reaction contacting time of 10 s, a reaction pressure of 0.4 MPa, a molar ratio of the CO gas I to butyl nitrite of 15:1; the operation conditions of the coupling reactor II are: a reaction temperature of 120° C., a reaction contacting time of 4.5 s, a reaction pressure of 0.05 MPa, a molar ratio of the CO gas II to the methyl nitrite effluent VII of 1.33:1. The results under the aforesaid conditions are: an NO utilizing efficiency of 99.3%, an amount of nitride oxides in the exhausted end gases of 6 ppm, a space time yield of dimethyl oxalate of 988 g/(h·L), and a selectivity of dimethyl oxalate of 99.2%.

Example 10

The procedures according to Example 1, but: the NO gas is a mixture gas with an NO volume percent of 95% and a nitrogen volume percent of 5%; the nitrogen entering the system balances the nitrogen exiting the system; the supergravity rotating bed reactor I and the coupling reactor I are not present; the NO gas is directly supplemented and mixed with the gas phase effluent IX containing NO; the constitution of the catalyst II by weight is 0.52% Pd++2.0% Mn/α-Al$_2$O$_3$. The operation conditions of the supergravity rotating bed reactor II are: a reaction temperature of 50° C., a reaction pressure of 0.01 MPa, a reaction contacting time of 4 s, a molar ratio of NO in the gas phase stream V containing NO to methanol and oxygen of 1:7:0.25; the operation conditions of the coupling reactor II are: a reaction temperature of 122° C., a reaction contacting time of 6 s, a reaction pressure of 0.05 MPa, a molar ratio of the CO gas II to the methyl nitrite effluent VII of 1.2:1. The results under the aforesaid conditions are: an NO utilizing efficiency of 99.0%, nitride oxides occupying 0.7% in the exhausted end gases, a space time yield of dimethyl oxalate of 960 g/(h·L), and a selectivity of dimethyl oxalate of 98.1%.

Example 11

The procedures according to Example 1, but: the NO gas is a mixture gas with an NO volume percent of 90% and a nitrogen volume percent of 10%; the nitrogen entering the system balances the nitrogen exiting the system; the supergravity rotating bed reactor I and the coupling reactor I are not present; the NO gas is directly supplemented and mixed with the gas phase effluent IX containing NO; the constitution of the catalyst II by weight is 0.32% Pd++2.0% Fe/α-Al$_2$O$_3$. The operation conditions of the supergravity rotating bed reactor II are: a reaction temperature of 40° C., a reaction pressure of 0.02 MPa, a reaction contacting time of 2 s, a molar ratio of NO in the gas phase stream V containing NO to methanol and oxygen of 1:8:0.25; the operation conditions of the coupling reactor II are: a reaction temperature of 130° C., a reaction contacting time of 6 s, a reaction pressure of 0.05 MPa, a molar ratio of the CO gas II to the methyl nitrite effluent VII of 1.4:1. The results under the aforesaid conditions are: an NO utilizing efficiency of 98.5%, nitride oxides occupying 0.6% in the exhausted end gases, a space time yield of dimethyl oxalate of 990 g/(h·L), and a selectivity of dimethyl oxalate of 99.0%.

Comparative Example 1

The same catalysts, conditions and reaction raw materials as those in Example 6, but: C$_2$-C$_4$ alkanol is replaced by methanol. The results are: an NO utilizing efficiency of 90.0%, nitride oxides occupying 1% in the exhausted end gases, a space time yield of dimethyl oxalate of 880 g/(h·L), and a selectivity of dimethyl oxalate of 95.4%.

Comparative Example 2

The same catalysts, conditions and reaction raw materials as those in Example 6, but: the supergravity rotating bed reactor I and the supergravity rotating bed reactor II are both replaced by the normal gravity fixed-bed reactors. The results are: an NO utilizing efficiency of 89.3%, nitride oxides occupying 0.9% in the exhausted end gases, a space time yield of dimethyl oxalate of 870 g/(h·L), and a selectivity of dimethyl oxalate of 94.1%.

Comparative Example 3

The same catalysts, conditions and reaction raw materials as those in Example 10, but: the supergravity rotating bed reactor II is replaced by the normal gravity fixed-bed reactor. The results are: an NO utilizing efficiency of 87.1%, nitride oxides occupying 1.5% in the exhausted end gases, a space time yield of dimethyl oxalate of 870 g/(h·L), and a selectivity of dimethyl oxalate of 95.0%.

According to the comparison results above, it is obvious that this invention achieves notable technical effects.

The invention claimed is:

1. A process of producing oxalate, comprising:
   i) subjecting a gas phase stream, methanol and oxygen, in a supergravity rotating bed reactor II, to an oxidative esterification reaction to produce an effluent VI, wherein the gas phase stream V comprises NO;
   ii) separating effluent VI to obtain an methyl nitride effluent VII;
   iii) contacting the methyl nitrite effluent VII and a CO gas II, in a coupling reactor II, with a catalyst II to form a dimethyl oxalate effluent VIII and a gas phase effluent IX comprising NO;
   iv) separating the dimethyl oxalate effluent VIII to obtain a dimethyl oxalate product stream I;
   v) optionally mixing the gas phase effluent IX with the gas phase stream V prior to entering the supergravity rotating bed reactor II;
   wherein the supergravity rotating bed reactor II comprises a rotor and the rotor has a porous filler layer attached thereto, wherein the catalyst II comprises Pd supported on a catalyst carrier and has a Pd amount of 0.01-1% based on a weight of elemental Pd relative to a weight of the catalyst carrier.

2. The process according to claim 1, further comprising, prior to step i),
   reacting a nitride oxide mixture and C2-C4 alkanol in the presence of air or oxygen to produce an effluent I;
   separating, from the effluent I, an incondensable gas effluent II and an effluent III comprising C2-C4 alkyl nitrite; and
   contacting the effluent III and a CO gas I, in a coupling reactor I, with a catalyst I to form an oxalate liquid phase effluent IV and the gas phase stream V;
   separating the oxalate liquid phase effluent IV to obtain an oxalate product II.

3. The process according to claim 2, wherein the supergravity rotating bed reactor I comprises a rotor and the rotor has a porous filler layer attached thereto, wherein a molar ratio of the CO gas II to the CO gas I is 5-300:1 and wherein the catalyst I comprises Pd supported on a catalyst carrier and has a Pd amount of 0.01-1% based on a weight of elemental Pd relative to a weight of the catalyst carrier.

4. The process according to claim 1, wherein the supergravity rotating bed reactor II has a reaction temperature of 20-100° C., a reaction pressure of −0.05-2.0 MPa, a reaction contacting time of 0.05-300 s, a molar ratio of NO in the gas phase stream V to methanol to oxygen of 1: 1-50:0.01-0.25.

5. The process according to claim 4, wherein the supergravity rotating bed reactor II has a reaction temperature of 25-70° C., a reaction pressure of 0.05-1.0 MPa, a reaction contacting time of 1-200 s, a molar ratio of NO in the gas phase stream to methanol to oxygen of 1:1-20:0.1-0.25.

6. The process according to claim 2, wherein the supergravity rotating bed reactor I has a reaction temperature of 20-100° C., a reaction pressure of −0.05-2.0 MPa, a reaction contacting time of 0.05-300 s, and a molar ratio of the nitride oxide mixture to the C2-C4 alkanol to oxygen in the air or oxygen of 1:1-50:0.2-0.3, and wherein the supergravity rotating bed reactor II has a reaction temperature of 20-100° C., a reaction pressure of −0.05-2.0 MPa, a reaction contacting time of 0.05-300 s, a molar ratio of NO in the gas phase stream V to methanol to oxygen of 1:1-50:0.01-0.25.

7. The process according to claim 6, wherein the supergravity rotating bed reactor I has a reaction temperature of 30-70° C., a reaction pressure of 0.01-1.0 MPa, a reaction contacting time of 1-200 s, and a molar ratio of the nitride oxide mixture to the C2-C4 alkanol to oxygen in the air or oxygen of 1:1-20:0.22-0.28, and wherein the supergravity rotating bed reactor II has a reaction temperature of 25-70° C., a reaction pressure of 0.05-1.0 MPa, a reaction contacting time of 1-200 s, and a molar ratio of NO in the gas phase stream V to methanol to oxygen of 1:1-20:0.1-0.25.

8. The process according to claim 1, wherein the coupling reactor II has a reaction temperature of 80-160° C., a reaction contacting time of 0.1-100 s, a reaction pressure of −0.05-2.0 MPa, and a molar ratio of the CO gas II to the methyl nitrite effluent VII of 1.1-10:1.

9. The process according to claim 8, wherein the coupling reactor II has a reaction temperature of 90-150° C., a reaction contacting time of 0.5-50 s, a reaction pressure of 0.01-1.0 MPa, and a molar ratio of the CO gas II to the methyl nitrite effluent VII of 1.1-5:1.

10. The process according to claim 2, wherein the coupling reactor I has a reaction temperature of 80-160° C., a reaction contacting time of 0.1-100 s, a reaction pressure of −0.05-2.0 MPa, and a molar ratio of the CO gas I to the C2-C4 alkyl nitrite of 1.1-15:1, and wherein the coupling reactor II has a reaction temperature of 80-160° C., a reaction contacting time of 0.1-100 s, a reaction pressure of −0.05-2.0 MPa, and a molar ratio of the CO gas II to the methyl nitrite effluent VII of 1.1-10:1.

11. The process according to claim 10, wherein the coupling reactor I has a reaction temperature of 90-150° C., a reaction contacting time of 0.5-50 s, a reaction pressure 0.01-1.0 MPa, and a molar ratio of the CO gas I to the C2-C4 alkyl nitrite of 1.1-10:1, and wherein the coupling reactor II has a reaction temperature of 90-150° C., a reaction contacting time of 0.5-50 s, a reaction pressure of 0.01-1.0 MPa, and a molar ratio of the CO gas II to the methyl nitrite effluent VII of 1.1-5:1.

12. The process according to claim 2, wherein the C2-C4 alkanol is selected from the group consisting of ethanol, propanol, butanol and a combination thereof.

13. The process according to claim 2, wherein the molar ratio of the CO gas II to the CO gas I is 10-200:1.

14. The process according to claim 2, wherein the amount of Pd in catalyst I is 0.01-0.8% based on the weight of elemental Pd relative to the weight of the carrier.

15. The process according to claim 14, wherein the amount of Pd in catalyst I is 0.02-0.6% based on the weight of elemental Pd relative to the weight of the carrier.

16. The process according to claim 1, wherein the amount of Pd in catalyst II is 0.01-0.8% based on the weight of elemental Pd relative to the weight of the carrier.

17. The process according to claim 16, wherein the amount of Pd in catalyst II is 0.02-0.6% based on the weight of elemental Pd relative to the weight of the carrier.

18. The process according to claim 2, wherein catalyst I and catalyst II each comprises Pd in an amount of 0.01-0.8% based on the weight of elemental Pd relative to the weight of the carrier.

19. The process according to claim 18, wherein catalyst I and catalyst II each comprises Pd in an amount of 0.02-0.6% based on the weight of elemental Pd relative to the weight of the carrier, respectively.

\* \* \* \* \*